United States Patent [19]
Elliott et al.

[11] Patent Number: 5,834,469
[45] Date of Patent: Nov. 10, 1998

[54] ENDOTHELIN RECEPTOR ANTAGONISTS

[75] Inventors: John Duncan Elliott, Wayne; Jack Dale Leber, Doylestown, both of Pa.

[73] Assignee: SmithKline Beecham Corporation, Philadelphia, Pa.

[21] Appl. No.: 737,852

[22] PCT Filed: Jun. 7, 1995

[86] PCT No.: PCT/US95/07904

§ 371 Date: Jun. 7, 1995

§ 102(e) Date: Jun. 7, 1995

[87] PCT Pub. No.: WO95/33752

PCT Pub. Date: Dec. 14, 1995

Related U.S. Application Data

[63] Continuation-in-part of Ser. No. 255,623, Jun. 9, 1994, abandoned.

[51] Int. Cl.$^6$ ..................... A61K 31/505; C07D 239/00
[52] U.S. Cl. ..................... 514/249; 514/258; 544/280; 544/350
[58] Field of Search ..................... 544/280, 350; 514/249, 258

[56] References Cited

U.S. PATENT DOCUMENTS

| | | | |
|---|---|---|---|
| 3,311,628 | 3/1967 | Partyka et al. | 544/280 |
| 3,382,245 | 5/1968 | Hansen et al. | 544/350 |
| 4,229,453 | 10/1980 | Roth et al. | 514/259 |
| 4,918,075 | 4/1990 | Zahler et al. | 514/262 |
| 5,098,905 | 3/1992 | Malone et al. | 514/258 |
| 5,244,896 | 9/1993 | Borcherding et al. | 514/258 |
| 5,248,775 | 9/1993 | Taylor et al. | 544/280 |
| 5,254,687 | 10/1993 | Taylor et al. | 544/280 |
| 5,281,708 | 1/1994 | Josyula et al. | 544/280 |
| 5,328,910 | 7/1994 | Hargreaves | 514/258 |
| 5,349,064 | 9/1994 | Akimoto et al. | 544/280 |
| 5,378,700 | 1/1995 | Sakuma et al. | 514/212 |
| 5,543,413 | 8/1996 | Townsend et al. | 514/258 |
| 5,650,511 | 7/1997 | Elliott et al. | 544/280 |

FOREIGN PATENT DOCUMENTS

| | | | |
|---|---|---|---|
| 705107 | 3/1965 | Canada . | |
| 705417 | 3/1965 | Canada | 260/262 |
| WO 88/03142 | 5/1988 | WIPO | C07D 487/04 |
| WO88/03142 | 5/1988 | WIPO . | |

OTHER PUBLICATIONS

Duffy et al., J. Chem. Soc., Perkins Transactions I, pp. 1921–1929, Oct. 1974.

Klumpp, Chemical Abstracts 111:19945, 1989.

Daly, Chemical Abstracts 109:221932, 1988.

Fokers, Chemical Abstracts 106:43451, 1986.

Steinhilber, Chemical Abstracts 106:27368, 1986.

Folkers, Chemical Abstracts 104:141712, 1985.

Dave et al., J. Indian Chem. Soc. vol. LXIV, No. 11, pp. 713–715, Nov. 1987.

Duffy, et al., "Pyrrolo[2,3–d]pyrimidines. Synthesis from 4–Pyrimidylhydrazones, a 2–Bis(methylthio)methyleneaminopyrrole–3–carbonitrile, and a Pyrrolo[2,3–d][1,3]thiazine–2(1H)–thione", *J. Chem. Society*, pp. 1921–1929 (1974).

*Primary Examiner*—Matthew V. Grumbling
*Attorney, Agent, or Firm*—Linda E. Hall; Stephen A. Venetianer

[57] ABSTRACT

The invention concerns compounds of the following formulae:

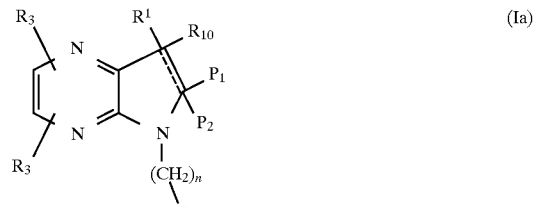

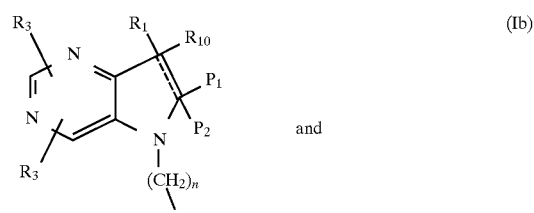

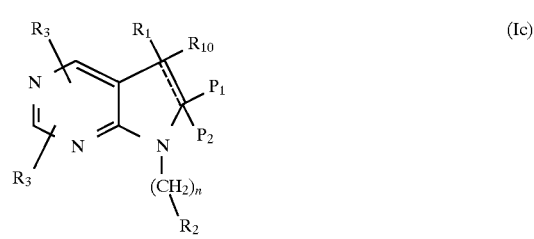

wherein the variables are defined in the specification. The compounds are useful as endothelin receptor antagonists.

7 Claims, No Drawings

ENDOTHELIN RECEPTOR ANTAGONISTS

This application claims priority under 35 U.S.C. §371 from PCT/US95/07904, filed 07 Jun. 1995, which is a CIP of U.S. application Ser. No. 08/255,623, filed 09 Jun. 1994, now abandoned.

FIELD OF THE INVENTION

The present invention relates to novel pyrrolopyrizine and pyrrolopyrimidine derivatives, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. *Br. J. Pharm.* 99: 597–601, 1989 and Clozel and Clozel, *Circ. Res.,* 65: 1193–1200, 1989) coronary vasospasm (Fukuda et al., *Eur. J. Pharm.* 165: 301–304, 1989 and Lüscher, *Circ.* 83: 701, 1991) heart failure, proliferation of vascular smooth muscle cells, (Takagi, *Biochem & Biophys. Res. Commun.;* 168: 537–543, 1990, Bobek et al., *Am. J. Physiol.* 258:408-C415, 1990) and atherosclerosis, (Nakaki et al., *Biochem. & Biophys. Res. Commun.* 158: 880–881, 1989, and Lerman etal., *New Eng. J. of Med.* 325: 997–1001, 1991). Increased levels of endothelin have been shown after coronary balloon angioplasty (Kadel et al., No. 2491 *Circ.* 82: 627, 1990).

Further, endothelin has been found to be a potent constrictor of isolated mammalian airway tissue including human bronchus (Uchida et al., *Eur J. of Pharm.* 154: 227–228 1988, LaGente, *Clin. Exp. Allergy* 20: 343–348, 1990; and Springall et al., *Lancet,* 337: 697–701, 1991). Endothelin may play a role in the pathogenesis of interstitial pulmonary fibrosis and associated pulmonary hypertension, Glard et al., Third International Conference on Endothelin, 1993, p. 3[4] and ARDS (Adult Respiratory Distress Syndrome), Sanai et al., Supra, p. 112.

Endothelin has been associated with the induction of hemorrhagic and necrotic damage in the gastric mucosa (Whittle et al., *Br. J. Pharm.* 95: 1011–1013, 1988); Raynaud's phenomenon, Cinniniello et al., *Lancet* 337: 114–115, 1991); Crohn's Disease and ulcerative colitis, Munch et al., *Lancet*, Vol. 339, p. 381; Migraine (Edmeads, Headache, Feb. 1991 p 127); Sepsis (Weitzberg et al., *Circ. Shock* 33: 222–227, 1991; Pittet et al., *Ann. Surg.* 213: 262–264, 1991), Cyclosporin-induced renal failure or hypertension (*Eur. J. Pharmacol.,* 180: 191–192, 1990, *Kidney Int,* 37: 1487–1491, 1990) and endotoxin shock and other endotoxin induced diseases (Biochem. Biophys. Res. Commun., 161: 1220–1227, 1989, *Acta Physiol. Scand.* 137: 317–318, 1989) and inflammatory skin diseases. (*Clin Res.* 41:451 and 484, 1993).

Endothelin has also been implicated in preclampsia of pregnancy. Clark et al., *Am. J. Obstet. Gynecol.* March 1992, p. 962–968; Kamor et al., *N. Eng. J. of Med.,* Nov 22, 1990, p. 1486–1487; Dekker et al., *Eur J. Ob. and Gyn. and Rep. Bio.* 40 (1991) 215–220; Schiff et al., *Am. J. Ostet. Gynecol.* Feb 1992, p. 624–628; diabetes mellitus, Takahashi et al., *Diabetologia* (1990) 33:306–310; and acute vascular rejection following kidney transplant, Watschinger et al., *Transplantation* Vol. 52, No. 4, pp. 743–746.

Endothelin stimulates both bone resorption and anabolism and may have a role in the coupling of bone remodeling. Tatrai et al. *Endocrinology,* Vol. 131, p. 603–607.

Endothelin has been reported to stimulate the transport of sperm in the uterine cavity, Casey et al., *J. Clin. Endo and Metabolism*, Vol. 74, No. 1, p. 223–225, therefore endothelin antagonists may be useful as male contraceptives. Endothelin modulates the ovarian/menstrual cycle, Kenegsberg, *J. of Clin. Endo. and Met.*, Vol. 74, No. 1, p. 12, and may also play a role in the regulation of penile vascular tone in man, Lau et al., *Asia Pacific J. of Pharm.,* 1991, 6:287–292 and Tejada et al., *J. Amer. Physio. Soc.* 1991, H1078–H1085. Endothelin also mediates a potent contraction of human prostatic smooth muscle, Langenstroer et al, *J. Urolog*, Vol. 149, p. 495–499.

Thus, endothelin receptor antagonists would offer a unique approach toward the pharmacotherapy of hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, heart failure, asthma, pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism and benign prostafic hypertrophy.

SUMMARY OF THE INVENTION

This invention comprises pyrrolopyrazine and pyrrolopyrimidine derivatives represented by Formula (Ia–Ic) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, benign prostatic hypertrophy, pulmonary hypertension, maigraine, heart failure, atherosclerosis, and as an adjunct in angioplasty for prevention of restenosis.

This invention further constitutes a method of treatment of disease caused by an excess of endothelin, which comprises administering to an animal in need thereof an effective amount of a compound of Formula (Ia–Ic).

DETAILED DESCRIPTION OF THE INVENTION

The compounds of this invention are represented by structural Formula (Ia–Ic):

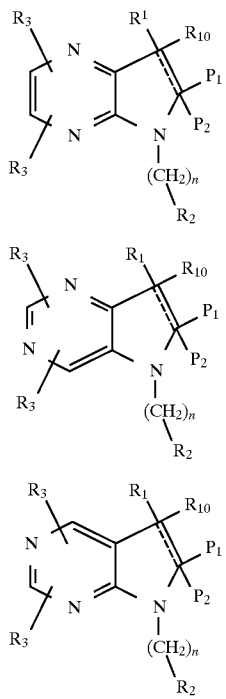

wherein:

$R_1$ is —$X(CH_2)_n Ar$ or —$X(CH_2)_n R_8$ or

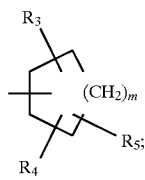

$R_2$ is Ar or (c);
$P_1$ is —$X(CH_2)_n R_8$;
$P_2$ is —$X(CH_2)_n R_8$, or —$XR_9 Y$;

$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, $NHCOR_6$, —$R_{12}CO_2R_7$, —$XR_9$—Y or —$X(CH_2)_n R_8$;

$R_4$ is hydrogen, $R_{11}$, OH, $C_{1-5}$alkoxy, $S(O)_q R_{11}$, $N(R_6)_2$, —$X(R_{11})$, Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-6}$alkyl or $(CH_2)_n Ar$;

$R_8$ is hydrogen, $R_{11}$, $CO_2R_7$, $PO_3H_2$, $P(O)(OH)R_7$, CN, —$C(O)N(R_6)_2$, tetrazole or $OR_6$;

$R_9$ is $C_{1-10}$alkylene, $C_{2-10}$alkenylene or phenylene all of which may be unsubstituted or substituted by one or more OH, $N(R_6)_2$, COOH, halogen or $XC_{1-5}$alkyl;

$R_{10}$ is $R_3$ or $R_4$;

$R_{11}$ is $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

$R_{12}$ is $C_{1-8}$ alkylene; $C_{2-8}$ alkenylene or $C_{2-8}$ alkynylene;

X is $(CH_2)_n$, O, $NR_6$ or $S(O)_q$;

Y is $CH_3$ or —$CH_2X(CH_2)_n Ar$;

Ar is:

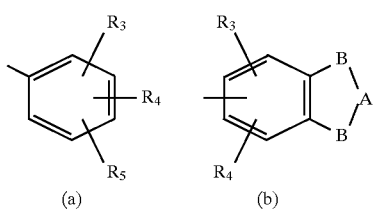

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or $(C(R_6)_2)_m$;

B is —$CH_2$— or —O—;

q is zero, one or two;

n is an integer from 0 to six;

m is 1, 2 or 3;

and the dotted line indicates the optional presence of a double bond; or a pharmaceutically acceptable salt thereof; provided that when the optional double bond is present there is no $P_1$ or $R_{10}$, and further provided that $P_1$ and $P_2$ are not methyl and $P_1$ and $P_2$ are not both hydrogen.

Also included in the invention are pharmaceutically acceptable salt complexes.

All alkyl, alkenyl, alkynyl, alkoxy, alkylene, alkenylene and alkynylene groups may be straight or branched. The term "halogen" is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

Preferred compounds are those wherein $R_1$ is $X(CH_2)_n Ar$, (Ar is (a) or (b)), dihydrobenzofuranyl, benzodioxanyl, cyclohexyl, or $C_{1-4}$alkyl; $R_2$ is (a), (b), indolyl or hydrogen; $R_3$ and $R_5$ are independently hydrogen, OH, $C_{1-5}$alkoxy, halogen, $R_{11}CO_2R_7$, $C_{1-4}$alkyl, $N(R_6)_2$, $NH(CO)CH_3$, —$X(CH_2)_nR_8$, -or $S(O)_pC_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_pC_{1-5}$alkyl; $P_1$ and $P_2$ are independently hydrogen, $CO_2H$ or tetrazole; Ar is (a), (b), or pyridyl; X is $(CH_2)_n$ or oxygen, and the double bond is present.

More preferred are compounds as above wherein $R_3$ is hydrogen or —$X(CH_2)_nR_8$, $R_{11}CO_2R_7$; $R_4$ and $R_5$ are independently hydrogen, OH, $C_{1-5}$alkoxy, $SC_{1-5}$alkyl, F, Br, $C_{1-3}$alkyl or $NH_2$.

Most preferred are compounds wherein $R_1$ and $R_2$ are independently 3,4 methylenedioxyphenyl (substituted or unsubstituted by a $C_{1-3}$ alkoxy or chloro group), phenyl substituted by one or two $C_{1-3}$ alkoxy, $O(CH_2)_n$ Ar or $O$—$(CH_2)_n$ $C(O)$ $N(H)$—$SO_2$—Ar groups wherein Ar is phenyl or pyridyl each of which may be substituted by $CO_2H$; $P_1$ is hydrogen, $P_2$ is $CO_2H$; the pyrimidine and pyrizine rings are unsubstituted and the double bond is present.

The present invention provides compounds of Formulae (Ia, Ib and Ic) above,

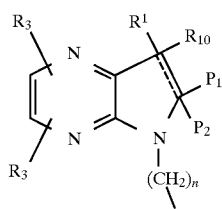

Ia

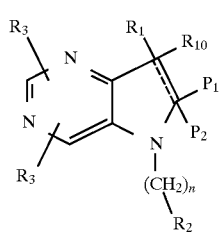

Ib

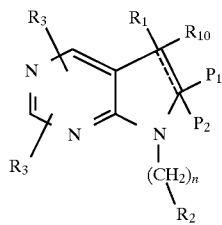

Ic which can be prepared by a process which comprises:
a) for compounds in which the optional double bond is present and there is no $R_{10}$ or $P_1$, reacting (as in this example for pyrrolo[3,2-d]pyrimidines) a compound of Formula (2),

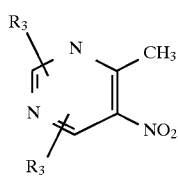

(2)

with the appropriate dialkyl oxalate in the presence of a base such as potassium ethoxide in a solvent such as tetrahydrofuran to provide a nitropyridine of formula (3).

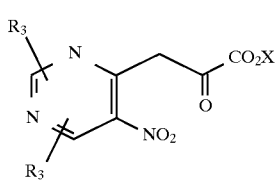

(3)

Reductive cyclization of compound (3) in the prescence of a catalyst, such as palladium on carbon, in a solvent such as ethyl alcohol under an atmosphere of hydrogen provides a pyrrolopyrimidine of formula (4)

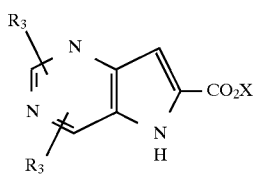

(4)

wherein X is $C_{1-5}$ alkyl. Reacting compound (4) with bromine in a suitable solvent such as dimethylformamide provides a bromopyrrolopyrimidine of Formula (5).

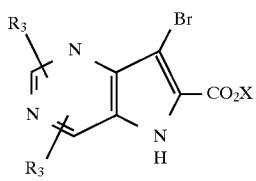

(5)

Coupling of Compound (5) with a boronic acid of formula (6):

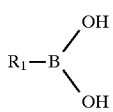

(6)

in the presence of a palladium (0) catalyst, such as tetrakis (triphenylphosphine)palladium (0), in a solvent such as toluene/methanol in the presence of a base such as aqueous sodium carbonate, at approximately 100° C., provides a pyrrolopyrimidine of Formula (7).

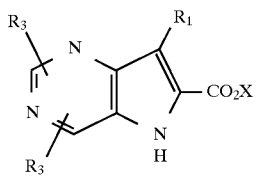

(7)

Aryl boronic acids of Formula (6) may be prepared by transmetallation of aryl halides of Formula (8):

(8)

wherein Hal is Cl, Br or I, with an alkyllithium, such as n-butyllithium in a solvent such as dry tetrahydrofuran at low temperature (−40° to −78° C.) followed by quenching with a trialkylborate, such as tri-isopropylborate, then treatment with an acid such as aqueous hydrochloric.

For compounds in which n is not 0, alkylation of a pyrrolopyrimidine of Formula (7) with an halide of Formula (9):

(9)

in a suitable solvent such as dimethylformamide or hexamethylphosphoramide in the presence of a suitable base such as sodium hydride affords compounds of Formula (10), n is not zero.

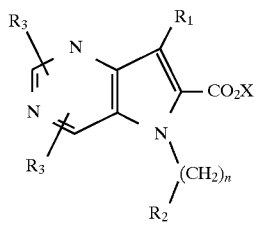
(10)

Saponification of esters of Formula (10) with aqueous sodium hydroxide in a solvent such as ethanol or isopropanol at reflux affords compounds of Formula (11), n is not zero.

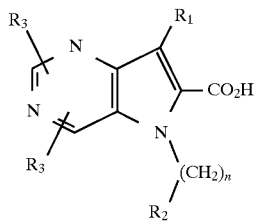
(11)

Alternatively, compounds of Formula (7) may be obtained by coupling of compound (5) with an aryl stannane derivative of Formula (12):

Ar—SnX$_3$ (12)

in the presence of a palladium (0) catalyst such as tetrakis (triphenylphosphine)palladium (0) in a solvent such as dioxan or dimethylformamide at approximately 100° C. in the presence of anhydrous lithium chloride. Aryl stannanes of Formula (12) may be prepared by transmetallation of aryl halides of Formula (8) with an alkyllithium, such as n-butyllithium, in a solvent such as tetrahydrofuran at low temperature (–40°--78° C.) followed by quenching with a trialkylchlorostannane of Formula (13).

Cl—SnX$_3$ (13)

b) As an alternative compounds of Formula (5) may be alkylated with a halide of Formula (9), n#0 in a suitable solvent such as dimethylformamide or hexamethylphosphoramide in the presence of a suitable base such as sodium hydride to afford compounds of Formula (14), n is not 0.

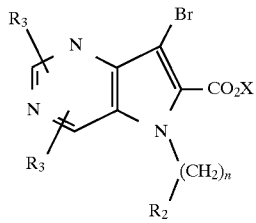
(14)

Coupling of Compound (14) with a boronic acid of formula (6) in the presence of a palladium (0) catalyst, such as tetrakis(triphenylphosphine)palladium (0), in a solvent such as toluene/methanol in the presence of a base such as aqueous sodium carbonate, at approximately 100° C., provides compounds of Formula (10) n is not zero.
As an alternative compounds of Formula (10), n is not zero, may be obtained by coupling of compound (14) with an aryl stannane derivative of Formula (12) in the presence of a palladium (0) catalyst such as tetrakis(triphenylphosphine) palladium (0) in a solvent such as dioxan or dimethylformamide at approximately 100° C. in the presence of anhydrous lithium chloride.

c) As a further alternative, pyrrolopyrimidines and pyrrolopyrazines may be prepared (as in this example for pyrrolo [2,3-d]pyrimidines) by a process which comprises:

alkylation of an ester of acetoacetic acid (15)

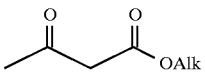
(15)

with a halide of Formula (16)

R$_1$—CH$_2$Hal (16)

in a suitable solvent such as acetonitrile and a base such as 1,8 diazabicyclo[5.4.0]undec-7-ene to afford compounds of Formula (17). Alternatively tetrahydrofuran may be used as the solvent and sodium hydride as the base for the alkylation.

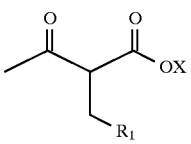
(17)

Treatment of a compound of type (17) with an aryl diazonium chloride of Formula (18)

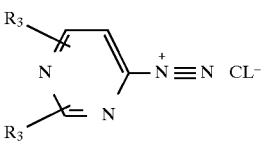
(18)

in a suitable solvent such as ethyl acetate in the presence of a base such as aqueous sodium hydroxide solution affords, by Japp-Klingemann rearrangement, hydrazones of Formula (19).

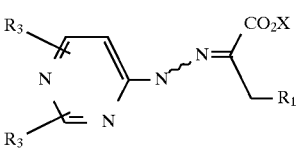
(19)

Thermal cyclisation of hydrazones of type (19) in a solvent such as ethylene glycol affords pyrrolo[2,3-b]pyrimidines of Formula (20)

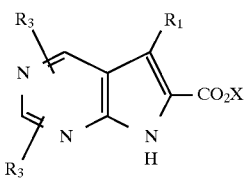
(20)

which can be alkylated similarly to compound (7) to provide compounds of formula (21).

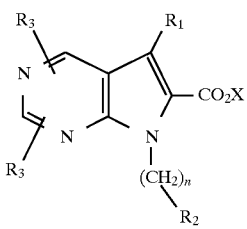

(21)

d) Compounds of type (1a–1c) where n=0–6 may be prepared as in this example for pyrrolo[2,3-d]pyrimidines by a process which comprises:

treatment of a compound of Formula (22)

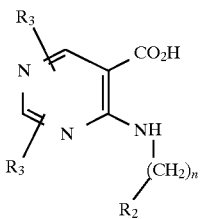

(22)

with aqueous formaldehyde solution at reflux affords a product of Formula (23).

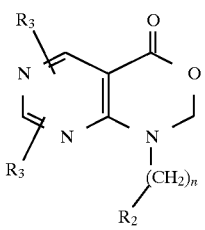

(23)

Treatment of compounds of type (23) with aqueous potassium cyanide at approximately 40°–50° C., affords nitriles of Formula (24).

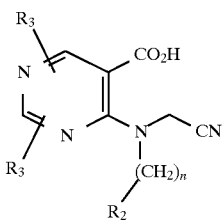

(24)

Hydrolysis of a nitrile of type (24) with aqueous sodium hydroxide at reflux followed by acidification with an acid such as hydrochloric affords diacids of Formula (25).

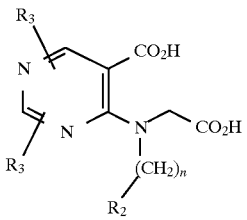

(25)

Diesterification of compounds of type (24) is achieved by treatment with a suitable base such as 1,8 diazabicyclo[5.4.0]undec-7-ene in a solvent such as acetonitrile or dimethylformamide followed by addition of iodomethane to afford compounds of Formula (26).

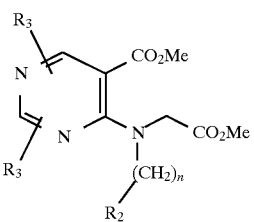

(26)

Dieckmann cyclization of diesters of type (26) using a base such as sodium methoxide and methanol as solvent at reflux affords products of Formula (27).

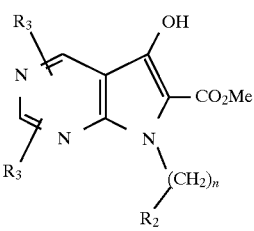

(27)

Treatment of compounds of type (27) with trifluoromethanesulfonic anhydride in pyridine as solvent affords triflates of Formula (28)

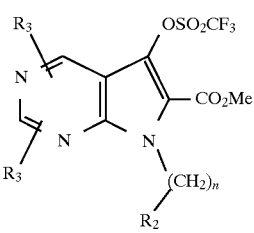

(28)

Compounds of Formula (21), X=Me, may be obtained by coupling of compound (28) with an aryl stannane derivative of Formula (12) in the presence of a palladium (0) catalyst such as tetrakis(triphenylphosphine)palladium (0) in a solvent such as dioxan or dimethylformamide at approximately 100° C. in the presence of anhydrous lithium chloride.

As an alternative compounds of Formula (21), X=Me, can be prepared by coupling of compound (28) with a boronic acid of formula (6) in the presence of a palladium (0) catalyst, such as tetrakis(triphenylphosphine)palladium (0), in a solvent such as toluene/methanol in the presence of a base such as aqueous sodium carbonate, at approximately 100° C.

Saponification of compounds of Formula (21), X=Me, to provides pyrrolo[2,3-d]pyrimidines-2-carboxylic acids of Formula (29) can be achieved by treatment with aqueous sodium hydroxide in a solvent such as ethanol or isopropanol at reflux.

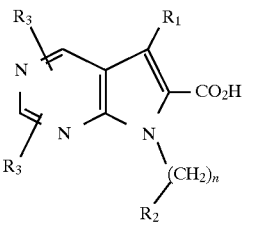

(29)

With appropriate manipulation and protection of any chemical functionalities, synthesis of the remaining compounds of the Formula (Ia–Ic) is accomplished by methods analogous to those above and to those described in the Experimental section.

In order to use a compound of the Formula (Ia–Ic) or a pharmaceutically acceptable salt thereof for the treatment of humans and other mammals it is normally formulated in accordance with standard pharmaceutical practice as a pharmaceutical composition.

Compounds of Formula (Ia–Ic) and their pharmaceutically acceptable salts may be administered in a standard manner for the treatment of the indicated diseases, for example orally, parenterally, sub-lingually, transdermally, rectally, via inhalation or via buccal administration.

Compounds of Formula (Ia–Ic) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1a–Ic) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (Ia–Ic) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (Ia–Ic).

The daily dosage regimen for oral administration is suitably about 0.01 mg/Kg to 40 mg/Kg, of a compound of Formula (Ia–Ic) or a pharmaceutically acceptable salt thereof calculated as the free acid. The daily dosage regimen for parenteral administration is suitably about 0.001 mg/Kg to 40 mg/Kg, of a compound of the Formula (Ia–Ic) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (Ia–Ic) are demonstrated by the following tests:

I. Binding Assay

A) Membrane Preparation (Rat cerebellum or kidney cortex)

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5mM EDTA, pH 7.5 at 4° C. using a motor-driven homogenizer. The homogenates were filtered through cheesecloth and centrifuged at 20,000×g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 micrograms of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 micrograms of membrane protein was used for each tube in binding experiments.

B) CHO Cell Membrane Preparation

CHO cells stably transfected with human $ET_A$ and $ET_B$ receptors were grown in 245 mm×245 mm tissue culture plates in Dulbecco's modified Eagle's medium (DMEM) supplemented with 10% fetal bovine serum (FBS). The confluent cells were washed with DPBS (Dulbecco's phosphate buffered saline) containing protease inhibitor cockatil (5 mM EDTA, 0.5 mM PMSF, 5 ug/ml leupeptin, and 0.1 U/ml aprotinin) and scraped in the same buffer. After centrifugation at 800×g, the cells were lysed by freezing in liquid nitrogen and thawing on ice followed by homogenization (30 times using glass dounce homogenizer) in lysis buffer containing 20 mM Tris HCl, pH 7.5 and the protease inhibitor cocktail. After an inititab centrifugation at 800×g for 10 min to remove unbroken cells and nuclei, the supernatants were centrifuged at 40,000×g for 15 min and the pellet was resuspended in 50 mM Tris HCl, pH 7.5 and 10 mM $MgCl_2$ and stored in small aliquots at −70° C. after freezing in liquid $N_2$. Protein was determined using BCA method and bovine serum albumin as the standard.

C) $[^{125}I]ET$-1 Binding Protocol $[^{125}I]ET$-1 binding to membranes from rat cerebellum (2–5 mg protein/assay tube) or kidney cortex (3–8 micrograms protein/assay tube) or CHO cell membranes (containing 4–6 and 1–2 micrograms of membrane protein for $ET_A$ and $ET_B$ receptors, respectively) were measured after 60 minutes incubation at 30° C. in 50 mM Tris HCl, 10 mM MgCl$_2$, 0.05% BSA, pH 7.5 buffer in a total volume of 100 microliters. Membrane p rotein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM MgCl$_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. IC$_{50}$'s for the compounds of this invention range from 0.01 nm to 50 uM.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; KH$_2$PO$_4$, 1.2; MgSO$_4$, 1.2; CaCl$_2$, 2.5; NaHCO$_3$, 25.0; and dextrose, 11.0. Tissue bath solutions are maintained at 37° C. and aerated continuously with 95% O$_2$/ 5% CO$_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET- 1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET- 1 induced vascular contractions are expressed as a percentage of the response elicited by 60 mM KCl for each individual tissue which is determined at the beginning of each experiment. Data are expressed as the mean±S.E.M. Dissociation constants (K$_b$) of competitive antagonists were determined by the standard method of Arunlakshana and Schild. The potency range for compounds of this invention range from 0.1 nM to 50 mm.

The following examples are illustrative and are not limiting of the compounds of this invention.

EXAMPLE 1

3-(4-Methoxyphenyl)-1-(3,4-methylenedioxyphenylmethyl) pyrrolo [2,3,-d] pyrimidine-2-carboxlic acid a) Ethyl 2-(4-methoxybenzyl)-3-oxobutyrate. A solution of ethyl acetoacetate and 4-methoxybenzyl chloride is stirred under an argon atmosphere with 1,8-diazabicyclo [5.4.0]undec-7-ene at room temperature in CH$_3$CN. The mixture is partitioned between 3N HCl and EtOAc The organic extract is washed successively with H$_2$O, maqueous NaHCO$_3$, H$_2$O and saturated aqueous NaCl and dried (Na$_2$SO$_4$). The solvent is removed in vacuo to afford the title compound.

b) Ethyl 3-(4-methoxyphenyl)pyrrolo[2,3]-pyrimidine-2-carboxylate. To a solution of ethyl 2-(4-methoxybenzyl)-3-oxobutyrate in EtOAc stirred at ice bath temperature under an argon atmosphere is added an aquious solution of NaOH. This is immediately followed by the addition of an aqueous solution of pyrimid-4-yldiazonium chloride [prepared from 4-aminopyrimidine in 6N HCl and NaNO2]. The mixture is partitioned between EtOAc and H$_2$O. The aqueous layer is washed with EtOAc. The combined organic extracts are washed with saturated aqueous NaCl solution, dried (Na$_2$SO$_4$) and the solvent is removed in vacuo. The residue is dissolved in ethylene glycol. This is refluxed then cooled to room temperature and partitioned EtOAc and H$_2$O. The aqueous layer is washed with EtOAc. The combined organic extract is washed with H$_2$O then saturated aqueous NaCl solution, dried (Na$_2$SO$_4$) and the solvent is removed in vacuo. The residue is purified by chromatography to afford the title compound.

c) Ethyl 1-(3,4-methylenedioxybenzyl)-3-(4-methoxyphenyl)pyrrolo[2,3-d]pyrimidine-2-carboxylate. To a solution of ethyl 3-(4-methoxyphenyl)pyrrolo[2,3-d] pyrimidine-2-carboxylate in HMPA stirred at ice bath temperature under an argon atmosphere is added NaH. A solution of piperonyl chloride in HMPA is added and the ice bath removed. The reaction mixture is stirred at room temperature then partitioned between 3N HCl and EtOAc. The organic extract is washed successively with H$_2$O, aqueous NaHCO$_3$, H$_2$O and saturated aqueous NaCl and dried (Na$_2$SO$_4$). The solvent is removed in vacuo. The residue is purified by chromatography to afford the title compound.

d) 1-(3,4-Methylenedioxybenzyl)-3-(4-methoxyphenyl)-pyrrolo[2,3-d]pyrimidine-2-carboxylic acid. A solution of ethyl 1-(3,4-methylenedioxybenzyl)-3-(4-methoxyphenyl) pyrrolo[2,3-b]pyrimidine-2-carboxylate in EtOH with aqueous 1N NaOH is stirred under an argon atmosphere first at room temperature then at reflux temperature. The reaction mixture is cooled to room temperature then poured into H$_2$O and the solvent volume reduced in vacuo. The aqueous solution is extracted with Et$_2$O and the Et$_2$O extract discarded. The aqueous layer is acidified with 6N HCl and the product extracted into EtOAc. The organic extract is washed with H$_2$O then saturated aqueous NaCl, dried (Na$_2$SO$_4$) and the solvent removed in vacuo to afford the title compound.

EXAMPLE 2

3-[2-(2-carboxyphenylmethoxy)-4-methoxy] phenyl-1 -(3,4-methylenedioxybenzyl) pyrrolo[2,3-d]pyrimidine-2-carboxylic acid

EXAMPLE 3

3-[4-methoxy-2-(N-phenylsulfonylcarboxammidomethoxy)phenyl]-1-(3, 4-methylenedioxybenzyl)pyrrolo[2,3-d]pyrimidine-2-carboxylic acid

EXAMPLE 4

Formulations for pharmaceutical use incorporating compounds of the present invention can be prepared in various forms and with numerous excipients. Examples of such formulations are given below.

Inhalant Formulation

A compound of formula Ia, Ib or Ic, (1 mg to 100 mg) is aerosolized from a metered dose inhaler to deliver the desired amount of drug per use.

| | Tablets/Ingredients | Per Tablet |
|---|---|---|
| 1. | Active ingredient (Cpd of Form Ia, Ib or IC) | 40 mg |
| 2. | Corn Starch | 20 mg |
| 3. | Alginic acid | 20 mg |
| 4. | Sodium alginate | 20 mg |
| 5. | Mg stearate | 1.3 mg |
| | | 2.3 mg |

Procedure for tablets:
Step 1 Blend ingredients No. 1, No. 2, No. 3 and No. 4 in a suitable mixer/blender.
Step 2 Add sufficient water portion-wise to the blend from Step 1 with careful mixing after each addition. Such additions of water and mixing until the mass is of a consistency to permit its converion to wet granules.
Step 3 The wet mass is converted to granules by passing it through an oscillating granulator using a No. 8 mesh (2.38 mm) screen.
Step 4. The wet granules are then dried in an oven at 140° F. (60° C.) until dry.
Step 5 The dry granules are lubricated with ingredient No. 5.
Step 6 The lubricated granules are compressed on a suitable tablet press.

Parenteral Formulation

A pharmaceutical composition for parenteral administration is prepared by dissolving an appropriate amount of a compound of formula 1a, 1b and or 1c in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of the formula (Ia, Ib and Ic)

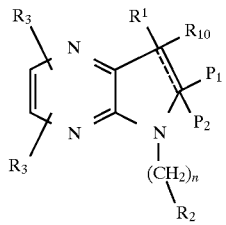
Ia

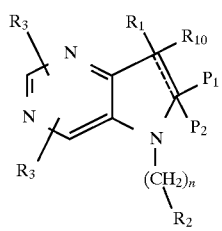
Ib

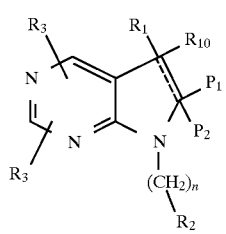
Ic wherein:
$R_1$ is —X(CH2)$_n$Ar
dihydrobenzofuranyl, benzodioxanyl, or cyclohexyl;

$R_2$ is Ar or (c);
$P_1$ is —X(CH$_2$)$_n$R$_8$;
$P_2$ is —X(CH$_2$)$_n$R, or —XR$_9$Y;
$R_3$ and $R_5$ are independently hydrogen, $R_{11}$, OH, $C_{1-8}$alkoxy, S(O)$_q$R$_{11}$, N(R$_6$)$_2$, Br, F, I, Cl, CF$_3$, NHCOR$_6$, —R$_{12}$CO$_2$R$_7$, —XR$_9$—Y or —X(CH$_2$)$_n$R$_8$;
$R_4$ is hydrogen, $R_{11}$, OH, $C_{1-5}$alkoxy, S(O)$_q$R$_{11}$,N(R$_6$)$_2$, —X(R$_{11}$), Br, F, I, Cl or NHCOR$_6$ wherein the $C_{1-5}$alkoxy may be unsubstituted or substituted by OH, methoxy or halogen;
$R_6$ is independently hydrogen or $C_{1-4}$alkyl;
$R_7$ is independently hydrogen, $C_{1-6}$alkyl or (CH$_2$)$_n$Ar;
$R_8$ is hydrogen, $R_{11}$, CO$_2$R$_7$, PO$_3$H$_2$, P(O)(OH)R$_7$, CN, —C(O)N(R$_6$)$_2$, tetrazole or OR$_6$;
$R_9$ is divalent $C_{1-10}$alkylene, $C_{2-10}$alkenylene or phenylene all of which may be unsubstituted or substituted by one or more OH, N(R$_6$)$_2$, COOH, halogen or XC$_{1-5}$alkyl;
$R_{10}$ is $R_3$ or $R_4$;
$R_{11}$ is monovalent or divalent $C_{1-8}$alkyl, $C_{2-8}$alkenyl, $C_{2-8}$alkynyl all of which may be unsubstituted or substituted by one or more OH, CH$_2$OH, N(R$_6$)$_2$ or halogen;
$R_{12}$ is $C_{1-8}$alkylene, $C_{2-8}$alkenylene or $C_{2-8}$alkynylene;
X is (CH$_2$)$_n$, O, NR$_6$ or S(O)$_q$;
Y is CH$_3$ or —CH$_2$X(CH$_2$)$_n$Ar;
Ar is:

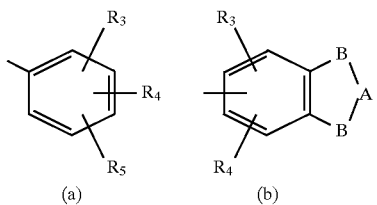

(a)    (b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;
A is C=O, or (C(R$_6$)$_2$)$_m$;
B is —CH$_2$— or —O—;
q is zero, one or two;
n is an integer from 0 to six;
m is 1, 2 or 3;
and the dotted line indicates the optional presence of a double bond; or a pharmaceutically acceptable salt thereof; provided that when the optional double bond is present there is no $P_1$ or $R_{10}$; and further provided that $P_1$ and $P_2$ are not methyl and $P_1$ and $P_2$ are not both hydrogen; and further provided that when $R_{11}$, $R_8$ or Y are Ar, the Ar is not substituted by another Ar which is further substituted by yet another Ar.

2. A compound of claim 1 wherein $R_2$ is (a), (b), or indolyl; $R_3$ and $R_5$ are independently hydrogen, OH, $C_{1-5}$alkoxy, halogen, $R_{11}$CO$_2$R$_7$, $C_{1-4}$alkyl, N(R$_6$)$_2$, NH(CO)CH$_3$, —X(CH$_2$)$_n$R$_8$, or S(O)$_p$C$_{1-5}$alkyl; $R_4$ is hydrogen, OH, $C_{1-5}$alkoxy, halogen, $C_{1-4}$alkyl, N(R$_6$)$_2$, NH(CO)CH$_3$ or S(O)$_p$C$_{1-5}$alkyl; $P_1$ and $P_2$ are independently hydrogen, CO$_2$H or tetrazole; $A_r$ is (a), (b) or pyridyl; and X is (CH$_2$)$_n$ or oxygen.

3. A pharmaceutical composition comprising a compound of claim 1 and a pharmaceutically acceptable carrier.

4. A method of treatment of diseases caused by an excess of endothelin comprising administering to a subject in need thereof, an effective amount to antagonize endothelin receptors of a compound of claim 1.

5. A method of treating hypertension which comprises administering to a subject in need thereof an effective amount of a compound of claim 1.

6. A method of treating renal failure which comprises administering to a subject in need thereof, an effective amount of a compound of claim 1.

7. A method of treating cerebrovascular disease which comprises administering to a subject in need thereof, an effective amount of a compound of claim 1.

\* \* \* \* \*